(12) United States Patent
Vespasiani

(10) Patent No.: US 11,793,410 B2
(45) Date of Patent: Oct. 24, 2023

(54) AUXILIARY COMPONENT FOR AN EQUIPMENT FOR CARDIAC AUTONOMIC NEUROPATHY TEST AND EQUIPMENT THAT INCLUDES SUCH A COMPONENT

(71) Applicant: METEDA S.r.l., San Benedetto del Tronto (IT)

(72) Inventor: Giacomo Vespasiani, San Benedetto del Tronto (IT)

(73) Assignee: METEDA S.R.L.

( * ) Notice: Subject to any disclaimer, the term of this patent is extended or adjusted under 35 U.S.C. 154(b) by 127 days.

(21) Appl. No.: 15/604,073

(22) Filed: May 24, 2017

(65) Prior Publication Data

US 2017/0340213 A1 Nov. 30, 2017

(30) Foreign Application Priority Data

May 27, 2016 (IT) ...................... 1020160000551393

(51) Int. Cl.
*A61B 5/087* (2006.01)
*A61B 5/0205* (2006.01)
(Continued)

(52) U.S. Cl.
CPC ........ *A61B 5/0205* (2013.01); *A61B 5/02438* (2013.01); *A61B 5/038* (2013.01);
(Continued)

(58) Field of Classification Search
CPC ..... A61B 5/0205; A61B 5/4035; A61B 5/682; A61B 5/741; A61B 5/7275;
(Continued)

(56) References Cited

U.S. PATENT DOCUMENTS

| | | | |
|---|---|---|---|
| 7,912,536 B2* | 3/2011 | Fendrock ........... | A61B 5/02405 600/484 |
| 2007/0088221 A1* | 4/2007 | Stahmann ............ | A61B 5/0215 600/485 |

(Continued)

FOREIGN PATENT DOCUMENTS

| | | |
|---|---|---|
| WO | 2015066562 A2 | 5/2015 |
| WO | 2016043601 A1 | 3/2016 |

OTHER PUBLICATIONS

Search Report and Written Opinion; Application No. IT UA2016003888; Completed: Feb. 3, 2017; 9 pages.

*Primary Examiner* — Eric J Messersmith
(74) *Attorney, Agent, or Firm* — Ware, Fressola, Maguire & Barber LLP

(57) ABSTRACT

Equipment for carrying out cardiac autonomic neuropathy tests includes a base unit to which a mouthpiece is connected, forming an autonomous system for measuring the pressure and/or the pattern of breath, provided with a series of LEDs aimed at informing a patient, who is undergoing the test, about correctness or incorrectness of a test execution. The mouthpiece is provided with a flow sensor, aimed at measuring a patient's pattern of breath, and a pressure sensor. The mouthpiece includes also an atmospheric pressure sensor aimed at measuring the environmental pressure. The equipment includes also a sensor, aimed at measuring the heartbeat, applied by simple contact to the patient's wrist area, and an orthostatic measuring device aimed at measuring any change of the patient's position. Data can be introduced or analysed and the type of exam to do can be selected. Results of the tests can be stored in a memory.

10 Claims, 1 Drawing Sheet

(51) Int. Cl.
  *A61B 5/03*    (2006.01)
  *A61B 5/00*    (2006.01)
  *A61B 5/024*   (2006.01)
  *A61B 5/097*   (2006.01)
  *G16H 50/20*   (2018.01)
  *G16H 40/63*   (2018.01)
  *A61B 5/11*    (2006.01)

(52) U.S. Cl.
  CPC ............ *A61B 5/0873* (2013.01); *A61B 5/097* (2013.01); *A61B 5/4035* (2013.01); *A61B 5/682* (2013.01); *A61B 5/7275* (2013.01); *A61B 5/741* (2013.01); *G16H 40/63* (2018.01); *G16H 50/20* (2018.01); *A61B 5/087* (2013.01); *A61B 5/1116* (2013.01); *A61B 5/742* (2013.01); *A61B 2560/0257* (2013.01); *A61B 2562/0247* (2013.01)

(58) Field of Classification Search
  CPC ... A61B 5/02438; A61B 5/097; A61B 5/0873; A61B 5/038; A61B 2560/0257; A61B 2562/0247; A61B 5/1116; A61B 5/087; A61B 5/742; G16H 40/63; G16H 50/20
  See application file for complete search history.

(56) References Cited

U.S. PATENT DOCUMENTS

| | | |
|---|---|---|
| 2009/0156952 A1 | 6/2009 | Hunter |
| 2017/0270260 A1* | 9/2017 | Shetty ................. A61B 5/6898 |
| 2018/0140252 A1* | 5/2018 | Luxon ................. A61B 5/0456 |

* cited by examiner

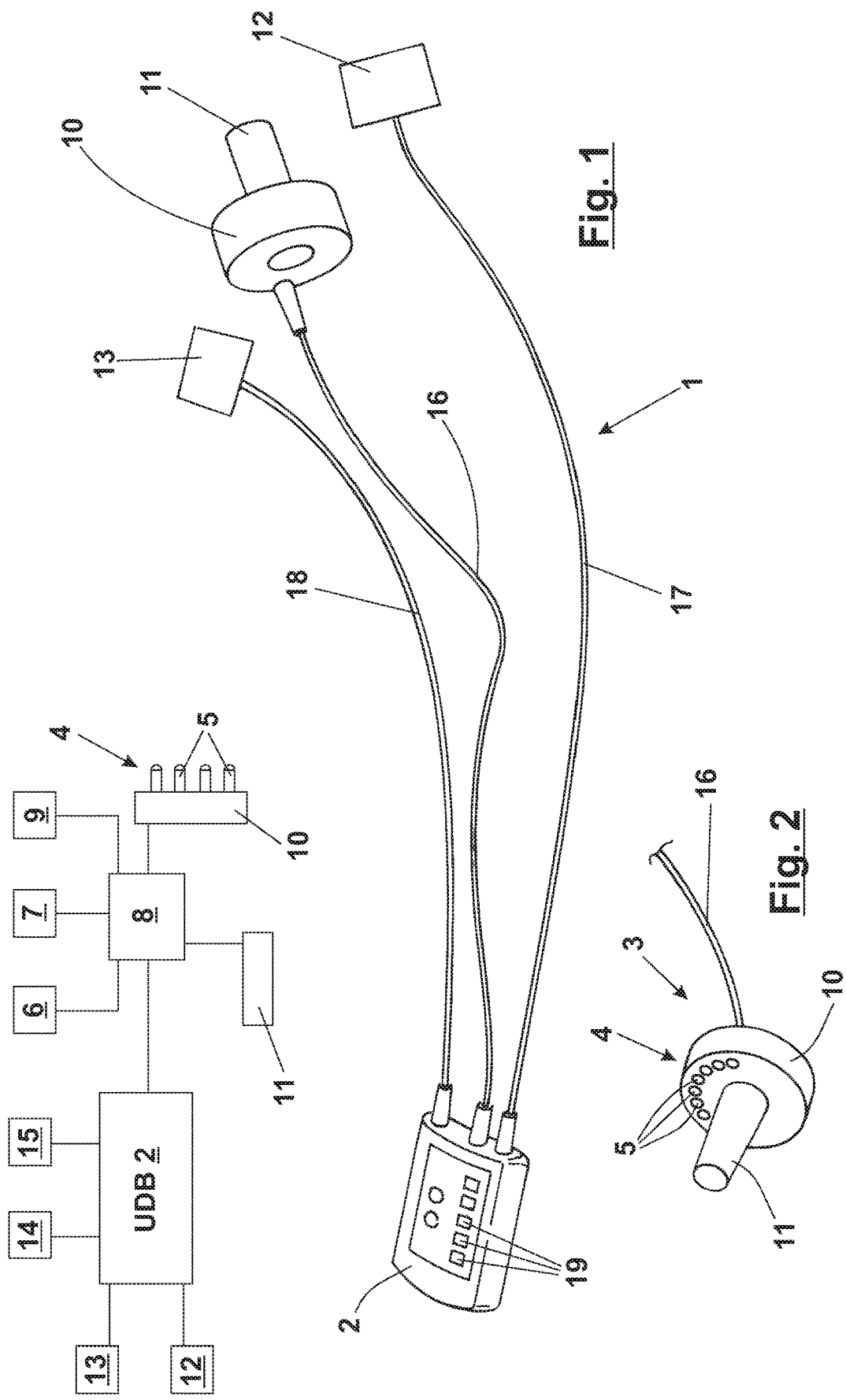

AUXILIARY COMPONENT FOR AN EQUIPMENT FOR CARDIAC AUTONOMIC NEUROPATHY TEST AND EQUIPMENT THAT INCLUDES SUCH A COMPONENT

BACKGROUND OF THE INVENTION

The present invention relates to electromedical devices which can be used autonomously by a patient at home and which allows periodical and easy execution, evaluations and tests of the state of health of users at home.

In particular, the present invention relates to an auxiliary component, hereinafter referred to as "mouthpiece" for sake of simplicity, which works together with an equipment for performing and calculating tests of cardiac autonomic neuropathy, with contemporary measurement of heartbeat, respiration, intrathoracic pressure and orthostatism, (hereinafter briefly referred to as "test equipment").

TECHNOLOGICAL BACKGROUND OF THE INVENTION

Equipments of the type described above have been known for a long time. They allow autonomous execution at home of a series of tests aimed at evaluating cardiovascular reflexes, as a standardised system for evaluation of the vegetative neuropathy, which can develop in diabetes patients.

The functionality of these equipments is aimed at routine diagnostics connected with the follow-up of the diabetic patient, which is generally carried out in diabetes departments and/or out-patient clinics as well as in neurological environment on patients affected by Parkinson's disease.

Some of the tests that can be carried out by the equipment include the one known as "Deep Breathing", which comprises an evaluation of changes in the heart rate during a series of deep respiratory cycles, "Lying to Standing", which allows an evaluation of the heart rate during rapid passages from a clinostatic position to an orthostatic one, and the "Valsalva manoeuvre", aimed at evaluating the heart rate during a persistent exhalation against a predetermined resistance. In the last test, a defined intrathoracic pressure must be reached during the exhalation.

If a person is performing a determined movement, for example he/she is performing certain physiological functions with an effort, or is passing from the lying position to the standing one, or is performing a series of deep breaths, in all these conditions, the heart beat frequency changes.

Performing these physiological functions, following a determined protocol which defines a standard way, causes a specific variation of the person's heart rate.

However, if such a person presents any problems associated with a certain autonomic neuropathy condition (sympathetic or parasympathetic), the variation of the heart rate will differ from the standard values.

Therefore, a different variation of the heart rate as a result of certain characteristic actions according to the predetermined standard parameters indicates problems associated with autonomic neuropathy.

It is obvious that a correct performing of such physiological actions, according to the defined standard parameters, is of the utmost importance for a correct evaluation and consequently a correct diagnosis.

Therefore, checking the way in which the patient performs the test is rather important and would normally require a physician capable of checking the correctness of the test execution.

Consequently, the only persons enabled to use the test equipment under discussion are medical and/or specialized nursing staff.

The equipment described above is able to carry out a verify, checking the breath pressure with respect to the heart rate, and to confirm the test correctness, thus allowing a less qualified person, for example a nurse, to perform the test.

In other words, the peculiar characteristic of such test equipment is that it can evaluate the quality of the test executed by the patient, concurrently monitoring the heartbeat, the second parameter that causes the heart rate variation (in the Deep Breathing test, the deepness of inhalation and exhalation, in the Valsalva manoeuvre, the intrathoracic pressure and in the Lying-to-Standing test, the moment of passage from the horizontal posture to the vertical one).

Other advantages made possible by this equipment are the automatic detection of extrasystoles on the basis of the variation of the QRS wave, the possibility of manual detecting the heartbeat to be used in the tests computing, and an automatic assessment of the test normality on the basis of the reference values stored in the system.

Moreover, the present equipment allows local and direct printing of a medical report (RR and second monitored parameter—breath—intrathoracic pressure—orthostatism), download of all tests performed on a computer and storing of 30-50 tests. The number of tests that can be stored depends substantially on the operational capacity and memory of the PC.

The known test equipment consists of:

a personal computer (PC), generally placed on a surface, for example a table, and supplied by the normal electric mains supply; an applied part called orthostatic "Satellite Unit", provided with a cable with three terminations, to be connected to disposable electrodes and a small pipe to be connected to a disposable filter, for pulmonary function. The personal computer and the satellite unit are connected to each other by Bluetooth connection. The disposable precordial electrodes must be applied to a patient in order to measure the heartbeat.

An operator inputs the patients' biographical data through a keyboard of the PC and a physician writes a report after having analysed resulting data.

A very important auxiliary component of the equipment is formed by the mouthpiece, which allows drawing a graph of a pattern of the patient's breath. The mouthpiece is provided with a special filter, for example a disposable Spirobac® Filter, but other types of materials can be used. The mouthpiece is connected to the small pipe so as to convey air emitted by the patient to the equipment.

In order to make the test equipment used so far function correctly, it is necessary to place the electrodes on the patient's left hemithorax, approximately along a straight line coinciding with the cardiac axis, in an explicitly indicated order.

When turned on, the PC displays an introductory window and then the necessary instructions for the equipment to be used, including a list of tests that can be executed.

For example, and in a simplified synthetic form, the choice of "Deep Breathing" displays a window divided in two horizontal bands. An upper band displays the patient's heartbeat as it is measured by the electrodes applied thereto, a lower band shows the evolution of the patient's breath as measured by the special mouthpiece.

In order to carry out this type of test, the patient must execute a cycle six times in succession. The cycle is composed of a deep inhalation, which lasts five seconds, followed by a complete exhalation of the same duration. The two inhalation and exhalation steps are marked by an acoustic sound, which helps the patient keep the rhythm of the breath steps.

During the test, the collected data are stored by the equipment in order to be processed afterwards and/or to be recovered. At the end of the test, the screen of the test analysis with the obtained results is automatically displayed.

When the test is completed, the program analyses the measured data and shows a screen divided in two bands, an upper one of which shows a graph corresponding to the heartbeat measured during the execution of the test, while a lower part shows the breathing cycle.

The two graphs (heartbeat and pressure) are synchronous and allow the operator to check the correct execution of the test. An evaluation of the check can be executed also afterwards, recovering the data stored in the memory directly in the equipment.

In any case, as already said, the correctness of the test can be evaluated by a physician having the necessary competence, but it is more difficult to evaluate by a nurse or even the patient himself/herself.

Then there are environmental conditions which can compromise the good result of the test, even if it seems to be executed correctly. For example, if the test is executed in the mountains, at an altitude considerably higher with respect to the calibration altitude of the equipment, then a differential measuring of the intrathoracic pressure with respect to the external pressure is considerably different, and can result in an erroneous evaluation of the patient's real condition, in particular in the Valsalva manoeuvre.

SUMMARY OF THE INVENTION

The object of the present invention is to provide a device that enables obtaining always a correct evaluation of the execution of the test being carried out by a biomedical equipment, in particular an equipment for carrying out and calculating cardiac autonomic neuropathy tests, with contemporary measurement of heartbeat, respiration, intrathoracic pressure and orthostatism.

The present invention proposes in particular a so called "smart" mouthpiece, which is capable of informing the patient or, if necessary, a nurse, about the correctness of the test execution.

Within this scope, it is an object of the invention to provide an equipment which is not affected by environmental variations, in particular of the pressure, when a difference between this measured parameter and a value measured in an external environment has a significant effect on the test results.

Therefore, another object of the invention is to simplify the test execution to such an extent that no particular expertise is necessary to execute it correctly. The possibility of checking the parameters characterizing the execution of the test afterwards allows in any case attesting its correctness.

Another object of the present invention is to obtain what has just been mentioned with a simple but efficient solution, which is reliable and does not require particular preparation and maintenance operations and which generally does not affect negatively the total costs of the equipment.

The above mentioned objects are obtained by an equipment for carrying out and calculating cardiac autonomic neuropathy tests, with contemporary measurement of heartbeat, respiration, intrathoracic pressure and orthostatism, composed of a mouthpiece and a base unit, with the mouthpiece being adapted to form an autonomous system for measuring pressure and/or trend of breath, provided with means aimed at informing a patient, who is undergoing the test, about correctness or incorrectness of the test performance, and connected to the base unit so as to transmit thereto data collected during the test and to receive therefrom instructions about the type of the selected test and a method for carrying it out.

BRIEF DESCRIPTION OF THE DRAWINGS

The characteristic features of the invention which do not result from what has been said above, will become evident from the following description, examined with reference to the table of drawings, in which:

FIG. 1 illustrates the equipment proposed by the present invention as a whole;

FIG. 2 illustrates the mouthpiece proposed by the present invention in a detailed way;

FIG. 3 is a simplified block diagram of the apparatus proposed by the present invention.

DETAILED DESCRIPTION OF EMBODIMENTS

With reference to the above Figures, the reference numeral 1 indicates an equipment proposed by the present invention, in particular an equipment for carrying out and calculating cardiac autonomic neuropathy tests, with contemporary measurement of heartbeat, respiration, intrathoracic pressure and orthostatism.

The present invention refers always to this particular type of equipment, bearing in mind, however, that the component proposed by the invention can be used in other types of biomedical equipment without departing from the scope of the invention.

The equipment 1 is composed mainly by a base unit 2, which contains the logics and electronic components necessary for operation of the equipment, not described in a detailed way, since they are not relevant to the object of the invention. Suffice it to say that the base unit may include hardware including one or more signal processors that include at least one central processing unit (CPU) and at least one memory device including software including a computer program that executes, at least in part, the procedures described herein. In order to understand the invention, it is enough to take into consideration such hardware including for instance a data processing board (not shown in the block diagram of FIG. 3).

The base unit 2 may be connected to a PC (personal computer) 14 by a wireless connection, for example a Bluetooth connection. The PC 14 may include at least one signal processor that includes at least one central processing unit (CPU) and at least one memory device including a computer program that executes, at least in part, the procedures described herein. The at least one memory may include one or more of random-access memory, dynamic random-access memory, read only memory, a hard drive, a flash drive, a solid-state drive, phase-change memory, etc. The PC can be used to input and analyse the data related to the test to execute. The PC 14 can be used also to select the type of exams to execute. The data acquired during the test are transmitted from the base unit 2 to the PC 14, where they are stored in the at least one memory. Such data will be available for a subsequent analysis and comparison with other data. As mentioned before in the introductory note, the equipment 1 can carry out the tests known as "Deep Breathing", which comprises an evaluation of any variation in the heart rate during a series of deep respiratory cycles, "Lying to Standing", which enables an evaluation of the heart rate during a rapid passage from a clinostatic position to an orthostatic one, and the "Valsalva manoeuvre", in which a detection of the pressure of the air exhaled by the patient is particularly important.

The type of test to be carried out is selected using one or more buttons 19 provided on an outer casing of the base unit 2 and connected to a processing board provided thereinside. Other buttons, provided on the base unit 2, activate and deactivate the equipment, start and/or stop the test execution, etc., in operating ways which are commonly used for this type of equipment.

An auxiliary component is connected to the base unit 2 by a cable 16. In particular, the auxiliary component consists of a mouthpiece (as it will be indicated hereinafter in the description) formed by a cylindrical container 10, whose function will become clear later on. An elongated cylindrical body 11 is partially embedded in the cylindrical container 10, and the patient has to blow into it during the test.

According to the invention, the mouthpiece 3, illustrated in FIG. 2 in a detailed way, constitutes an autonomous system for measuring the pressure and/or the pattern of breath, and is provided with means 4 aimed at informing the patient, who is undergoing the test, about the correctness of the test execution. In the same way, the means 4 inform the patient about possible incorrectness in the test execution.

The mouthpiece 3 is connected to the base unit 2 so as to transmit thereto data acquired during the test and to receive therefrom instructions about the type of the selected test and the method for carrying it out.

In a more detailed way, a flow sensor 6 is placed inside the mouthpiece 3, in the cylindrical container 10, and is aimed at measuring the patient's pattern of breath, and a pressure sensor 7, aimed at measuring the pressure of the breath being given out. A flow sensor can be, without limitation, a fiber optic air flow sensor or fiber-based humidity or temperature sensors, among other flow monitoring devices. A pressure sensor can for instance be a piezoresistive transducer (monolithic silicon pressure sensor) with an analog output that is proportional to the applied pressure and read into an analog-to-digital input of a microcontroller. There is a large variety of pressure sensors and force collective types are suitable such as those mentioned below.

The values of the patient's breathing cycle and/or pressure of the breath measured by the sensors 6 and 7 are sent to an electronic processing board 8, situated likewise inside the cylindrical container 10 to process the obtained values in order to evaluate the correctness of the test execution.

For the cases in which the evaluation of the pressure is of a crucial importance for the results of the test, for example during the "Valsalva manoeuvre", the mouthpiece 3 comprises also an atmospheric pressure sensor 9, adapted to measure the environmental pressure. As mentioned above, there is a large variety of pressure sensors and force collective types are suitable. These include, without limitation, piezoresistive strain gauge, capacitive, electromagnetic, piezoelectric, optical, and potentiometric. Other types, such as resonant and thermal are possible.

The atmospheric pressure sensor 9 is connected to said processing electronic board 8 for the evaluation of the correctness of the test execution depending also on the atmospheric pressure that is present locally.

Therefore, if the test is carried out in a place of considerably high altitude, the software running on the processing electronic board 8 will calculate the difference between the pressure measured locally and the calibration pressure of the equipment, thus assuring the reliability of the test.

Once the correctness of the test has been checked, for example, verifying that the patient's respiratory cycles and/or the pressure with which the breath is given out correspond to those provided in the protocol, allowing, if necessary, for the variation of the pressure with respect to the calibration data, the mouthpiece informs the patient about the correctness or incorrectness of the test execution by means 4.

In the exemplifying embodiment illustrated herein (FIG. 2), such means 4 include a series of coloured LEDs 5, which indicate the correct carrying out of the test with a predetermined combination of lights in accordance with the instructions received from said base unit 2.

As illustrated by way of example in FIG. 1, the LEDs 5 are arranged on a surface of the cylindrical container 10 of the mouthpiece 3, for example, along an arc of a circle. The number of LEDs being on, for example green, gives information about the execution of the test; for example, the whole arc being on means "correct execution", while only a part of LEDs or no LED being on, or only a part of LEDs being green and the remaining ones being red, indicate that the execution of the test is not correct. For example, the breathing is too quick or the pressure is insufficient for a correct evaluation of the state.

The parameters necessary for the evaluation of the correctness of the test execution are determined on the basis of instructions, corresponding to the type of the test each time selected, received by the base unit 2 from the PC 14, and on the basis of which the operation of the mouthpiece is adapted.

The equipment proposed by the present invention, whose block diagram is illustrated in FIG. 3, includes also sensor means 12 aimed at measuring the heartbeat and connected to the base unit 2 through a corresponding cable 17. Such may include a set of electrode leads, optics using infrared light, conductive smart fabric with built-in microprocessors, etc. For instance, the skin may be illuminated by a small lamp or LED and the amount of light transmitted or absorbed measured to sense a change in blood volume caused by a pressure pulse of the cardiac cycle. The heart rate data is essential for calculating the parameters to be sent to the mouthpiece 3 for the evaluation of the correctness of the test being performed.

Yet the heart rate is also one of the essential data for the test results. Indeed, the measured heart rate, processed by a suitable software program together with the measured parameters of breath frequency/pressure, is displayed on a screen, associated with the equipment by a cable or a wireless connection (e.g. Bluetooth or WiFi) together with the parameters measured by the mouthpiece 3, according to the techniques which are already well settled in the execution of this test.

However, according to the embodiment illustrated herein, the sensor means 12 are applied by contact to the patient's wrist area, and not by conventional electrodes applied by adhesion to the patient's chest (suction cups, adhesive plates, etc.).

This considerably simplifies the preparation of the equipment 1 to carry out the test, making it easy to be used by anyone.

In order to complete the data possibly necessary for the test, the equipment 1 can include also orthostatic measuring means 13, connected to said base unit 2 by a respective cable 18, aimed at measuring the change of the patient's position. Some examples for the orthostatic measuring means 13 are: a) one or more simple "mercury bubble" switches (if more than one, operating on different axes of orientation), that open or close an electric contact when their inclination changes; b) one or more accelerometers, that can detect and measure the patient's acceleration when he changes his position in as many degrees of freedom as needed. Both of these kind of sensors are very common and widely used. If necessary, the measured orthostatic parameters are also used both to obtain the test results and to determine the operation data of the mouthpiece 3, since also the variation of the position is an important parameter for the evaluation of the test execution.

The measurements and data processed during the test execution are then stored in the memory of the PC 14, to be examined or referred to subsequently, if necessary, for comparison or other uses, which will be evident for those skilled in the art.

Thus, the auxiliary component of FIG. 1 comprises a mouthpiece forming, together with a base unit, a biomedical test equipment, in particular an equipment for carrying out and calculating cardiac autonomic neuropathy tests, with contemporary measurement of heartbeat, respiration, intrathoracic pressure and orthostatism, wherein said mouthpiece forms an autonomous system for measuring a pressure or a trend of breath, or both, including means aimed at informing a patient undergoing said test about correct or incorrect performance of the test, the mouthpiece being connected to the base unit so as to transmit data collected during the test to the base and to receive instructions about the test and a method for carrying it out from the base unit.

The various hardware/software components described above together carry out the procedural steps described above. Those steps may be expressed as a combination of computer instructions and data definitions that enable a computer such as a central processing unit of a PC 14 shown in FIG. 3 to perform acts of computation or control. Thus, such instructions may take the form of a program. Such software is sometimes referred to as comprising computer program code that likewise comprises computer instructions and data definitions expressed in a programming language or in a form output by an assembler, compiler, or other translator. Such computer program code is thus able, together with at least one central processing unit, to cause the system at least to carry out certain steps such as outlined above in whole or in part. Such method steps as described herein may be coded by a computer programmer so as to express the method steps in a programming language. In an exemplary embodiment, the equipment 1 may be a portable device such as shown but may take other forms. Such a portable device may carried by a user as the user travels and is moreover typically used, once the user is settled, in a handheld manner with the user holding the device in at least one hand in such a way that the display LEDs face the face of the user for comfortable viewing while blowing into the erlongated cylindrical body. The user of the equipment of FIG. 1 may carry out the procedures described above by way of actuating one or more of the buttons 19 in the base unit 2 at the time of the test.

Another embodiment might have the base unit in the form of a computing device such as a laptop, a tablet, or smart phone with a similar informational interface provided by way of a downloadable application ("app") and with the laptop, tablet or smart phone communicating with a device such as a device similar to that of FIG. 2 except perhaps modified to display the informational content of the LEDs on the laptop, tablet or smartphone. In any event, a laptop, tablet or smartphone is a mobile or portable electronic computer with a display, circuitry and a battery, typically in a single unit. It comes equipped with various sensors not necessarily relevant to the present invention but can also be made to communicate, for instance wirelessly, with medical sensors such the device of FIG. 2, as described herein. In that sense, a wireless connection would replace the cables 16, 17, 18 of FIG. 1. The tablet or smartphone may include one or more physical buttons to control certain functions such as on, off, audio volume, and silencing. Most include a jack for insertion of a headphone or earphone plug but if not, wireless connectivity is instead provided for audio communications. Many include one or more ports for network communications, to charge the battery, or to insert a flash memory card or stick. On-screen features may include a pop-up touchscreen keyboard for typing. A touch input allows the user to navigate easily and type with a virtual keyboard on the screen. The tablet or smartphone responds to the touches, which allows integrated hand-eye operation by the user. Known touchscreen hardware includes resistive and capacitive touchscreens. Known tablets or smartphones include the Apple iPad and the Apple iPhone that operate using the Apple operating system. Tablets of other manufacturers such as the Samsung Galaxy, Kindle Fire and the Nook run the Android operating system provided by Google as do many portable smartphones. Tablets are usually larger than smartphones with screens that may be 7 inches (diagonally) or larger. Smartphones also operate under the Apple and Android operating systems and have hardware similar to that described above for tablets. Tablets may also be equipped with stands so that the tablet may be temporarily supported on a surface such as table for hands-free usage. A tablet or a smartphone may thus be supported or hand-held and handled by a user to operate the portable electronic device. Such an exemplary portable electronic display device may include a user input interface arrangement that is responsive to receiving a user input. Such a user input might be made by a finger or stylus touching a touch sensitive screen surface (touchscreen) of an electronic display, e.g. a display capable of displaying images such as stills or video or instructional text coupled with audio as well as stills or video. Known displays include a liquid crystal display (LCD), a light-emitting diode display (LED), an organic light emitting diode display (OLED), etc. The user input device of such an apparatus may condition the sensed touch input and send a signal over a bus to a signal processor that includes the above mentioned at least one CPU and the at least one memory device. The received touch input from the user may select an application displayed as an icon on the screen of the display of the exemplary portable electronic display device. When the user is performing the tests with the portable electronic display device in the vicinity of the user, e.g., held in the hand or hands of the user, the screen is visible to the user and imagery/audio/video is presented via the application and is viewable by the user. In response to the user input, an application launch signal may be generated by the signal processor. If the application is stored on a Read Only Memory (ROM), the application launch signal may be used internally within the signal processor to launch the application. Or, it could be transmitted to a memory device that may have the executable code for running the application stored therein. The launch of the application causes the application to be presented on the screen. In an embodiment, it may then prompt the user to input information corresponding to a test.

The prompted user may then enter information pertaining to the test. This may be done at the time of the test but may be done in advance of the user performing the test. In any event, a user input of information is received and, in response, the apparatus provides at least one information signal indicative of the user input of information. Again, this may be provided within the signal processor or to another device such as a data storage device or even external to the apparatus via a transceiver. The data storage may for instance be a hard disk drive, a flash memory device, non-volatile RAM, or any suitable non-volatile storage medium that stores digital data. The transceiver includes both a transmitter and a receiver which are combined to share common circuitry or a single housing. If no circuitry is common, it is a transmitter-receiver. If it is a radio frequency (RF) transceiver, RF circuitry modules are included for high speed data transmission. Such circuitry may convert between digital baseband signals and analog RF signals in a digital-RF architecture. Transceivers are called Medium Attachment Units (MAUs) in IEEE 802.3 standard specifications. The transceiver may instead be a modem which is similar to a transceiver, except that it uses modulation and demodulation for transmitted and received signals, respectively. The transceiver may instead be a transponder or transceiver that converts between a full-duplex electrical signal and a full-duplex optical signal, depending on whether the interface is parallel or serial, respectively. It is also possible for a wavelength conversion to be carried out with e.g. two transceivers placed back to back. Other transceiver-like interfaces are possible as well.

In a more developed embodiment, the equipment 1 includes also a speech synthesis or vocal synthesis system 15 intended for emitting acoustic instructions and information for the patient or the assistant who is using it. Such a system may include a computer program that takes ASCII or otherwise coded text items as an input and converts the text to audio items by means of a speech synthesis algorithm or using a pre-recorded table for words or phonemes. These programs are known and widely used.

The advantages which can be obtained by the invention are obvious. Using the technical solutions proposed by the invention, a device is obtained that allows to always have a correct evaluation of the tests carried out with the biomedical equipment for carrying out and calculating cardiac autonomic neuropathy tests, with contemporary measurement of heartbeat, respiration, intrathoracic pressure and orthostatism.

In particular, the so-called "smart" mouthpiece, is capable of informing the patient or, if necessary, a nurse who helps him/her, about the correctness of the test execution. This causes a substantial simplification of the test execution, allowing it to be carried out by a specially trained nurse or even the patient himself/herself.

The possibility of checking afterwards the parameters characterizing the execution of the test allows in any case to attest its correctness.

Moreover, the equipment obtained in accordance with the invention is not affected by environmental variations, in particular by the pressure, when the difference between this measured parameter and the value measured in the external environment has a significant effect on the test results. This function is handled autonomously and automatically by the equipment on the basis of the test chosen to be carried out.

Finally, the invention is carried out by a simple but effective solution, which is reliable and does not require particular preparation and maintenance operations and which does not affect negatively the total costs of the equipment.

It is understood that what above has been described as a pure and not limiting example. Therefore, possible changes and variants of the invention are considered within the protective scope granted to the present technical solution, as described above and claimed below.

What is claimed is:

1. An auxiliary component comprising test equipment for carrying out and calculating cardiac autonomic neuropathy tests, with contemporary measurement of heartbeat, respiration, intrathoracic pressure and orthostatism said auxiliary component including a mouthpiece and a base unit, wherein
said mouthpiece forms an autonomous system for measuring a pressure, or a trend of breath, or both, said mouthpiece including light emitting diode (LED) means aimed at informing a patient undergoing a selected test about correct or incorrect performance of the selected test, said mouthpiece being connected to said base unit so as to transmit data collected during the selected test to said base unit and to receive instructions about the selected test and a method for carrying it out from said base unit, said mouthpiece further comprising
a flow sensor aimed at measuring a trend of breath of said patient, and a pressure sensor aimed at measuring a pressure of the breath being given out, as well as a processing electronic board for processing obtained values for estimating correctness of performance of said selected test, wherein
the processing is carried out in said base unit or in a computer via said base unit according to stored test instructions concerning the selected test that include parameters on the basis of which the correctness of performance of the selected test is considered and on the basis of which operation of said auxiliary component is adjusted, wherein said means aimed at informing the patient about the correctness of performance of said selected test include a series of LEDs, more than three in number, said series of LEDs indicating a correct performance of the test with a predetermined combination of lights in accordance with instructions received from or via said base unit wherein said series of LEDs are arranged on a surface of a cylindrical container containing, partially incorporated therein, an elongated cylindrical body, said elongated cylindrical body forming, together with said cylindrical container, said mouthpiece, wherein said cylindrical container has a cylindrical surface bounded by two bases, wherein the elongated cylindrical body is partially incorporated in one base of said two bases, wherein said elongated cylindrical body has a smaller diameter than a larger diameter of said one base, wherein said surface of the cylindrical container that said LEDs are arranged on an annular surface of said one base, said annular surface having an inside diameter defined by said smaller diameter of said elongated cylindrical body and an outside diameter defined by said larger diameter of said one base, and wherein said LEDs are arranged in a semicircular arc on said one base around said elongated cylindrical body so as to be face-to-face with the patient blowing into the mouthpiece via said elongated cylindrical body for comfortable viewing.

2. The auxiliary component in accordance with claim 1, wherein said mouthpiece further comprises an atmospheric pressure sensor for measuring an environmental pressure, said atmospheric pressure sensor being connected to said processing electronic board for an evaluation of correct performance of the selected test depending on the atmospheric pressure locally present.

3. The auxiliary component in accordance with claim 1, said component further comprising sensor means aimed at measuring the heartbeat in order to communicate a measured heart rate signal to said base unit for processing and calculation of parameters for an evaluation of correct performance of the test, said sensor means being applied by simple contact in a patient's wrist area, said measured heart rate signal communicated via a cable connected to the base unit.

4. The auxiliary equipment in accordance with claim 3, further comprising orthostatic measuring means connected to said base unit via a separate cable, for communicating a signal to said base unit indicative of a change in position of the patient.

5. The auxiliary equipment in accordance with claim 4, wherein the heart rate is processed by means of a suitable software program made operative in said base unit or in a computer connected to said base unit, together with measured parameters of at least one of breath frequency or pressure, or both, and orthostatic parameters, in order to obtain test results.

6. The auxiliary equipment in accordance with claim 3, wherein said base unit is connectable to said computer by means of a wired or wireless connection, for input and analysis of data and selection of type of exam to perform, and for storing measurements obtained during the test in a memory of said computer, and with a vocal synthesis system designed to emit acoustic instructions and information for the patient or an assistant who is using the equipment.

7. The auxiliary component in accordance with claim 1, wherein a longitudinal axis of the cylindrical container coincides with a longitudinal axis of the elongated cylindrical body.

8. The auxiliary component in accordance with claim 7, wherein said base unit is connected to the mouthpiece by a cable connection for transmitting a sensed flow signal, a sensed pressure signal, and a sensed atmospheric pressure signal.

9. The auxiliary component in accordance with claim 2, wherein said base unit is connected to the mouthpiece by a cable connection for transmitting a sensed flow signal, a sensed pressure signal, and a sensed atmospheric pressure signal from said mouthpiece to said base unit.

10. An auxiliary component comprising test equipment for carrying out and calculating cardiac autonomic neuropathy tests, with contemporary measurement of heartbeat, respiration, intrathoracic pressure and orthostatism said auxiliary component including a mouthpiece and a base unit, wherein said mouthpiece forms an autonomous system for measuring a pressure, or a trend of breath, or both, said mouthpiece including light emitting diode (LED) means aimed at informing a patient undergoing a selected test about correct or incorrect performance of the selected test, said mouthpiece being connected to said base unit so as to transmit data collected during the selected test to said base unit and to receive instructions about the selected test and a method for carrying it out from said base unit said mouthpiece further comprising a flow sensor aimed at measuring a trend of breath of said patient, and a pressure sensor aimed at measuring a pressure of the breath being given out, as well as a processing electronic board for processing obtained values for estimating correctness of performance of said selected test, wherein the processing is carried out in said base unit or in a computer via said base unit according to stored test instructions concerning the selected test that include parameters on the basis of which the correctness of performance of the selected test is considered and on the basis of which operation of said auxiliary component is adjusted, wherein said means aimed at informing the patient about the correctness of performance of said selected test include a series of LEDs, more than three in number, said series of LEDs indicating a correct performance of the test with a predetermined combination of lights in accordance with instructions received from or via said base unit, wherein said series of LEDs are arranged on a surface of a cylindrical container containing, partially incorporated therein, an elongated cylindrical body, said elongated cylindrical body forming, together with said cylindrical container, said mouthpiece, wherein said LEDs are arranged in a semicircular arc on said cylindrical container around said elongated cylindrical body so as to be face-to-face with the patient blowing into the mouthpiece via said elongated cylindrical body for comfortable viewing of said LEDs.

* * * * *